USOO5695996A

United States Patent [19]
Quinn et al.

[11] Patent Number: 5,695,996
[45] Date of Patent: Dec. 9, 1997

[54] ARTIFICIAL ORGAN CULTURE SYSTEM

[75] Inventors: Frederick D. Quinn, Decatur; Kristin A. Birkness, Atlanta, both of Ga.

[73] Assignee: The United States of America as represented by the Department of Health and Human Services, Washington, D.C.

[21] Appl. No.: 311,762

[22] Filed: Sep. 23, 1994

[51] Int. Cl.$^6$ ........................................... C12N 5/08
[52] U.S. Cl. .................... 435/367; 435/371; 435/402; 435/325; 435/1.1
[58] Field of Search .................. 435/1, 240.241, 435/240.242, 240.2, 1.1, 401, 402, 325, 367, 371

[56] References Cited

PUBLICATIONS

Marieb, *Human Anatomy and Physiology*, Benjamin/Cummings Publishing Co., Inc., 1992, pp. 792–796.

Weyant et al., "Human Microvascular Endothelial Cell Toxicity Caused by Brazilian Purpuric Fever–Associated Strains of *Haemophilus Influenzae* Biogroup Aegyptius," *The J. of Infect. Dis.*, 169:430–433 (1994).

Alexander et al., "Low density lipoprotein uptake by an endothelial–smooth muscle cell bilayer," *J. of Vasc. Surg.*, 13(3):444–451 (Mar., 1991).

Graham et al., "Aortic Endothelial and Smooth Muscle Cell Co–Culture: An In Vitro Model of the Arterial Wall," *J. of Investig. Surg.*, 4:487–494 (1991).

Shaw et al., "Model for Invasion of Human Tissue Culture Cells by *Neisseria gonorrhoeae*," *Infect and Immun.*, 56(6):1625–1632 (Jun., 1988).

van Buul–Wortelboer et al., "Reconstitution of the Vascular Wall In Vitro: A Novel Model to Study Interactions between Endothelial and Smooth Muscle Cells," *Exp. Cell. Res.* 162:2–9 (1986).

Zinman et al., "Cell Culture of Embryonic Chick Duodenal Cells: Preparation of Epithelial–Fibroblast Bilayers and Homotypic Cultures of Fibroblasts and Epithelial Cells," *J. Pediatr. Gastroenterol. Nutr.*, vol. 4(1):107–117 (1985).

Stephens et al., "Interaction of *Neisseria meningitidis* with Human Nasopharyngeal Mucosa: Attachment and Entry into Columnar Epithelial Cells," *J. Infect. Dis.*, 148(3):369–376 (Sep., 1983).

Birkness et al. "a Tissue Culture Bilayer Model to Study the Passage of *Neisseria meningitidis*" *Inf. and Immun.* 63(2):402–409, Feb. 1995.

Freshney, R. "Culture of Animal Cells, A Manual of Basic Techniques" 2nd Ed. A.R. Liss, Inc., New York, 1987, pp. 297–307.

*Primary Examiner*—John W. Rollins
*Assistant Examiner*—Francisco C. Prats
*Attorney, Agent, or Firm*—Jones & Askew

[57] ABSTRACT

The present invention provides an artificial organ system comprising an endothelial cell layer, an epithelial cell layer and an artificial microporous membrane disposed between and indirect contact with the endothelial cell layer and epithelial cell layer such that the membrane has an endothelial side and an epithelial side. Also provided is a method of constructing an artificial organ system, comprising the steps of placing an artificial microporous membrane into a tissue culture well and supporting the membrane a selected distance from a bottom of the well to create an upper and lower chamber in the well such that the membrane has an endothelial side facing the bottom of the well and an opposite epithelial side; placing endothelial cells into the upper chamber of the well under conditions such that the endothelial cells form a confluent layer of cells on the epithelial side of the membrane; and placing epithelial cells into the upper chamber of the well under conditions such that the endothelial cells migrate through pores in the membrane and attach to the endothelial side of the membrane to form a confluent layer of endothelial cells on the endothelial side of the membrane and the epithelial cells form a confluent layer of epithelial cells on the epithelial side of the membrane.

10 Claims, No Drawings

ARTIFICIAL ORGAN CULTURE SYSTEM

BACKGROUND OF THE INVENTION

1. Field of the Invention

The present invention relates to an artificial organ system comprising an endothelial cell layer and an epithelial cell layer oriented on either side of and in direct contact with an artificial microporous membrane. The present invention also relates to methods for constructing the artificial organ system and for studying the passage of pathogens and chemical substances through the artificial organ system.

2. Background Art

*Meningococcal meningitis* continues to be a serious health problem worldwide. The etiologic agent, *Neisseria meningitidis*, has caused recent epidemics in South America, Africa, and the Middle East and remains a principal cause of morbidity and mortality in young children in developing countries where the disease is endemic (2). It is expected that global dissemination of outbreak associated strains will become even more common as international travel increases (18). Pharyngeal carriage of *Neisseria meningitidis* is common, but the mechanism by which the organism penetrates the mucosal surface and enters the bloodstream is still largely unknown. A number of animal models have been used to study the many facets of meningococcal pathogenesis including monkeys (8), chicken embryos (5), mice (10, 12), neonatal mice (15), genetic variant mice deficient in lipopolysaccharide (LPS) response (32), and guinea pigs with subcutaneous-implanted chambers (3). While these models have been useful in answering many experimental questions, the fact that *Neisseria meningitidis* is an exclusively human pathogen limits the relevance of animal models in the study of its pathogenesis.

The nasopharyngeal organ culture system developed by Stephens et al. (23) permits study of the interaction between bacteria and the intact mucosal surface as it would occur in a natural infection. However, these tissues are difficult to obtain, are variable from donor to donor, require the initial use of antibiotics, and have limited viability. In order to study the infectious process, a large inoculum (e.g., $10^6$ diplococci) must be used in the organ culture. Human buccal epithelial cells have been used by many researchers to study attachment of meningococci (16, 20); these cells are readily available, but vary greatly in age, size and viability.

Mammalian tissue culture monolayers have also been used extensively in the study of neisserial pathogenesis. These studies have employed HeLa human cervical carcinoma cells (4, 14), HecIB human endometrial carcinoma cells (19), Chang conjunctival cells (26), HEp-2 larynx carcinoma cells (30), and human umbilical vein endothelial cells (28). Monolayer studies have added much to current knowledge about meningococcal attachment and invasion. However, when infecting the human host, the bacterium is required to react with multiple cell layers clearly not present in a monolayer. Thus, there exists a need for a model that incorporates the added complexity of the cell-to-cell interaction associated with multiple layers.

The present invention meets this need by providing an artificial organ system incorporating epithelial and endothelial monolayers on a microporous membrane to examine the process of attachment and passage that occur as a bacterium makes its way from the mucosal surface through the epithelial cells and into the vascular system. The present invention was created fortuitously and unexpectedly. The inventors were originally attempting to culture a layer of epithelial cells directly on top of a layer of endothelial cells. Previous attempts to accomplish this had resulted in the epithelial cells outgrowing the endothelial cells (33). The inventors attempted to overcome the overgrowth problem by first establishing a layer of endothelial cells on an artificial microporous membrane suspended in a tissue culture well in the hope that nutrients in the fluid medium would remain accessible to the endothelial cells even after the epithelial cell layer was established on top of the endothelial cell layer. It was reasoned that greater exposure to nutrients might prevent the underlying endothelial cell layer from being starved and killed by the epithelial cells. Quite unexpectedly, upon addition of epithelial cells to the layer of endothelial cells growing on the membrane, the endothelial cells migrated through the pores of the membrane and grew into a layer of cells on the opposite side of the membrane, effectively establishing stable layers of two different cell types in very close proximity to one another.

This organization of cells allows the two different cell types to communicate and interact as they might in vivo. The system is easier to obtain and to use than any of the animal models, and, by making use of human cells, is more relevant to the pathogenesis of an exclusively human disease. The present system is consistently reproducible without the variability inherent in human buccal cells and nasopharyngeal organ cultures. The system can be maintained without the use of antibiotics and remains both viable and usable for a longer period of time than other systems. The infectious process can be studied in the present system using a much lower inoculum than in the organ culture system ($10^3$ vs $10^6$ diplococci).

Thus, the present artificial organ system is a useful model for the study of the attachment and invasion factors contributing to meningococcal pathogenesis and lends itself to similar studies with other microbial pathogens. Also, mutants and epidemic and sporadic case and carrier strains can be examined as they pass through the bilayer to determine which genes are turned on or off in response to changes in the environment and changes in the requirements for bacterial survival.

SUMMARY OF THE INVENTION

The present invention provides an artificial organ system comprising an endothelial cell layer, an epithelial cell layer and an artificial microporous membrane disposed between and in direct contact with the endothelial cell layer and epithelial cell layer such that the membrane has an endothelial side and an epithelial side. The present invention also provides an artificial organ system is contained in a vessel.

Also provided is a method of constructing an artificial organ system, comprising the steps of placing an artificial microporous membrane into a tissue culture well and supporting the membrane a selected distance from a bottom of the well to create an upper and lower chamber in the well such that the membrane has an endothelial side facing the bottom of the well and an opposite epithelial side; placing endothelial cells into the upper chamber of the well under conditions such that the endothelial cells form a confluent layer of cells on the epithelial side of the membrane; and placing epithelial cells into the upper chamber of the well under conditions such that the endothelial cells migrate through pores in the membrane and attach to the endothelial side of the membrane to form a confluent layer of endothelial cells on the endothelial side of the membrane and the epithelial cells form a confluent layer of epithelial cells on the epithelial side of the membrane.

The present invention further provides a method for determining the transport rate of pathogens through an artificial organ system comprising the steps of placing pathogens in contact with the artificial organ system under conditions such that the pathogens enter or pass through or between the epithelial cells and migrate through the membrane and into or through or between the endothelial cells; and determining the number of pathogens present on the endothelial side of the membrane, the number of pathogens providing a measure of the transport rate of the pathogens through an artificial organ system. Also provided is a method for determining transport mechanisms of pathogens through an artificial organ system comprising the steps of placing pathogens in contact with the artificial organ system under conditions such that the pathogens enter or pass through or between the epithelial cells and migrate through the membrane and into or through or between the endothelial cells; processing the artificial organ system for examination of the presence of the pathogens within the artificial organ system with a microscope; and observing the pathogens within the artificial organ system in a microscope in order to determine the characteristics of the transport mechanisms of the pathogens.

The present invention also provides a method for determining the transport rate of chemical substances through an artificial organ system comprising the steps of placing a chemical substance in contact with the artificial organ system under conditions such that the chemical substance enters or passes through or between the epithelial cells, passes through the membrane and into or through or between the endothelial cells; and determining the amount of the chemical substance present on the endothelial side of the membrane, the amount of chemical substance providing a measure of the transport rate of the chemical substance through an artificial organ system. Also provided is a method for determining transport mechanisms of chemical substances through an artificial organ system comprising the steps of placing a chemical substance in contact with the artificial organ system under conditions such that the chemical substance enters or passes through or between the epithelial cells and passes through the membrane and into or through or between the endothelial cells; processing the artificial organ system for examination of the presence of the chemical substance within the artificial organ system with a microscope; and observing the chemical substance within the artificial organ system in a microscope in order to determine the characteristics of the transport mechanisms of the chemical substance.

DESCRIPTION OF THE PREFERRED EMBODIMENTS

The present invention may be understood more readily by reference to the following detailed description of specific embodiments and the Examples included herein.

The present invention provides an artificial organ system comprising an endothelial cell layer, an epithelial cell layer and an artificial microporous membrane disposed between and in direct contact with the endothelial cell layer and the epithelial cell layer such that the membrane has an endothelial side and an epithelial side. By being in direct contact with the artificial microporous membrane, the endothelial cell layer and the epithelial cell layer are separated by a distance no greater than the thickness of the membrane, which can range from 10 to 200 microns.

As used herein, "endothelial cell" means a human or other (e.g. bovine) cell which lines the blood and lymphatic vessels and various other body cavities (34). Human endothelial cells are preferred because they are more relevant for the study of human disease and chemical transport in humans. Human endothelial cells can include the human microvascular endothelial cell line, HMEC-1 (CDC, Atlanta, Ga.) and the human umbilical cord cell line, HUV-EC-C (ATCC No. CRL 1730). Numerous non-human endothelial cells are publicly available and can be used to study various pathogens, particularly non-human pathogens. As used herein, "epithelial cell" means a human or other cell which forms the outer surface of the body and lines organs, cavities and mucosal surfaces (34). For example, such epithelial cells can comprise the human endometrial carcinoma cell line, HecIB (ATCC No. HTB 112), the human cervical carcinoma cell line, HeLa (ATCC No. CCL 2), the human lung carcinoma cell line, A549 (ATCC No. CCL 185) and the human larynx carcinoma cell line, Hep2 (ATCC No. CCL 23), among others. Numerous non-human epithelial cells are publicly available and can be used to study various pathogens, particularly non-human pathogens. As used herein, "layers" means confluent sheets of cells having a thickness of one cell or several cells.

As used herein, "endothelial side" means the surface of the membrane upon which the endothelial cell layer is growing. As used herein, "epithelial side" is the surface of the membrane upon which the epithelial cell layer is growing.

As used herein, an "artificial microporous membrane" means a membrane having a thickness of between 10 and 200 microns, with a preferable thickness range between 15 and 30 microns and pores of fairly uniform size within the membrane ranging in diameter from 0.45 microns to 10 microns, most preferably having a diameter of 3 microns. The membrane can be composed of a biactually stretched fluoropolymer or any material suitable for generating a track etch capillary pore membrane. For example, the membrane can be composed of polycarbonate, polytetrafluoroethylene, polyester, nitrocellulose, cellulose acetate, polycarbonate or polystyrene, among others. The membrane can also be coated on one or both sides with a biocompatible material to facilitate adhesion of cells to the membrane surfaces. This coating can consist of collagen, laminin, proteoglycan, vitronectin, fibronectin, poly-D-lysine or polysaccharides, among others, such as are available from Biocoat Cell Environments, Collaborative Biomedical Products, Becton Dickinson, Bedford, Mass.

The membrane can be supported a selected distance from the bottom of the tissue culture well by any of the well known means. The membrane can be supported by a supporting means, for example a plastic frame, such that the membrane can be suspended in a tissue culture well and such that the plastic frame forms a chamber around the membrane into which fluids can be placed. For example, the membrane can be built into a Transwell-COL™ insert (Costar, Cambridge, Mass.). Alternative supporting means can include wire baskets or supports made from gels, among others. The membrane can be supported above the bottom of the well by any distance between as long as the membrane can be covered by a fluid medium within the tissue culture well and a sufficient amount of space exists between the endothelial cell layer and the bottom of the well to allow nutrients in the fluid medium to contact the endothelial cell layer. Other biocompatible support means either known or subsequently developed can be used to support the membrane.

The present invention also provides a method of constructing an artificial organ system, comprising the steps of: (a) placing an artificial microporous membrane into a tissue culture well and supporting the membrane a selected distance from a bottom of the well to create an upper and lower chamber in the well such that the membrane has a basal surface (endothelial side) facing the bottom of the well and an opposite apical surface (epithelial side); (b) following step (a) and preceding step (c), placing endothelial cells into the upper chamber of the well under conditions such that the endothelial cells form a confluent layer of cells on the apical surface of the membrane; and placing epithelial cells into the upper chamber of the well under conditions such that the endothelial cells migrate through pores in the membrane and attach to the basal surface of the membrane to form a confluent layer of endothelial cells on the basal surface of the membrane and the epithelial cells form a confluent layer of epithelial cells on the apical surface of the membrane.

The present artificial organ system can be contained in a vessel. As used herein, "tissue culture well" means any of a variety of well known vessels for containing tissue cultures. For example, such vessels can be in the form of vials, bottles, tubes, chambers, flasks, single well plates or multiple well plates of glass, metal or plastic.

As used herein, "basal surface" means that side of the membrane which faces the bottom of the tissue culture well and is, thus, oriented downward. Also as used herein, "apical surface" means that side of the membrane facing away from the bottom of the well and is, thus, facing upward. In the completed artificial organ system, the apical surface and the epithelial side will coincide and the basal surface and the endothelial side will coincide.

The conditions under which the epithelial cells form a confluent layer of cells on the apical surface of the membrane can, for example, comprise maintaining the endothelial cells and artificial microporous membrane in endothelial basal medium with about 7.0% fetal bovine serum at about 37° C. in about 5.0% carbon dioxide for about eight days. Other physiologically balanced medium can be used, providing it contains adequate growth factors for endothelial cells. The medium can contain from 0 to 20% fetal bovine serum. The cells can be incubated at temperatures ranging from 25° C. to 42° C. and a concentration of carbon dioxide ranging from 2% to 8%. The endothelial cells can be cultured for six to ten days.

The conditions under which the epithelial cells are placed in contact with the endothelial cells such that the endothelial cells migrate through the pores of the membrane and attach to the basal surface of the membrane and form a confluent layer of endothelial cells on the basal surface of the membrane and the epithelial cells form a confluent layer of cells on the apical surface of the membrane can, for example, comprise maintaining the cells in endothelial basal medium with about 7.0% fetal bovine serum at about 37° C. in about 5.0% carbon dioxide for 15–20 days. Other physiologically balanced medium can be used, providing it contains adequate growth factors for endothelial cells and epithelial cells (e.g. Eagle's minimum essential medium). The medium can contain from 0 to 20% fetal bovine serum. The cells can be incubated at temperatures ranging from 25° C. to 42° C. and a concentration of carbon dioxide ranging from 2% to 8%.

The artificial organ system is also a useful way to screen chemicals (drugs, medicaments) to determine their movement through the bilayer. Such studies can also provide useful information on the effectiveness of applications such as drug treatments and vaccines whose mechanism of action involves blocking the binding of certain pathogens to host cells.

The artificial organ system can also be constructed by placing an artificial microporous membrane into a tissue culture well such that a surface of the membrane is oriented upward; placing endothelial cells into the well under conditions such that the endothelial cells form a confluent layer of cells on this surface of the membrane; inverting the membrane in the well and supporting the membrane a selected distance from the bottom of the well to create an upper and lower chamber in the well such that the surface containing the endothelial cells is now oriented downward and is the basal surface and a fresh surface is oriented upward and is the apical surface. Epithelial cells can then be placed into the upper chamber of the well under such conditions that the epithelial cells form a confluent layer of cells on the upward facing surface of the membrane.

The present invention also provides a method for determining the transport rate of pathogens through an artificial organ system comprising the steps of: (a) placing pathogens in contact with the artificial organ system of the present invention under conditions such that the pathogens enter or pass through or between the epithelial cells and migrate through the membrane and into or through or between the endothelial cells; and (b) determining the number of pathogens present on the endothelial side of the membrane or in the medium from the lower chamber, the number of pathogens providing a measure of the transport rate of the pathogens through an artificial organ system. The number of pathogens can be determined by removing the medium from the lower chamber and spreading the medium onto agar plates to determine the number of viable bacteria present. Alternatively, other standard cell counting means can be routinely applied.

Also provided in the present invention is a method for determining transport mechanisms of pathogens through an artificial organ system comprising the steps of: (a) placing pathogens in contact with the artificial organ system of the present invention under conditions such that the pathogens enter or pass through or between the epithelial cells and migrate through the membrane and into or through or between the endothelial cells; (b) processing the artificial organ system for examination of the presence of the pathogens within the artificial organ system with a microscope; and (c) observing the pathogens within the artificial organ system by microscope in order to determine the characteristics of the transport mechanisms of the pathogens.

An additional asset of this bilayer system is its potential adaptability for the study of a wide variety of organisms. Several epithelial cell lines have been used as the second layer in this system, including Chang conjunctival cells, which have been used to show differences between a virulent and an avirulent strain of *Haemophilus influenzae* biogroup aegyptius. For any organism to be examined, it is routine to construct an artificial organ system, as described herein, using physiologically relevant epithelial and endothelial cell lines. The endothelial layer can be a different vascular line, such as human umbilical vein cells, perhaps more relevant to the pathogenesis of a given organism. Immunological factors (e.g. antibodies or phagocytic cells) can be introduced into the system to examine the infectious process in an environment even more closely resembling what the organism encounters in vivo.

The present invention also provides a method for determining the transport rate of chemical substances through an artificial organ system comprising the steps of:(a) placing a chemical substance in contact with the artificial organ system under conditions such that the chemical substance enters or passes through or between the epithelial cells, passes through the membrane and into or through or between the endothelial cells; and b) determining the amount of the chemical substance present on the endothelial side of the membrane, the amount of chemical substance providing a measure of the transport rate of the chemical substance through an artificial organ system. The amount of the chemical substance can be determined by assaying the medium in the lower chamber according to protocols suitable for measurement of the given chemical substance in a fluid medium.

The present invention further provides a method for determining transport mechanisms of chemical substances through an artificial organ system comprising the steps of: (a) placing a chemical substance in contact with the artificial organ system under conditions such that the chemical substance enters or passes through or between the epithelial cells and passes through the membrane and into or through or between the endothelial cells; (b) processing the artificial organ system for examination of the presence of the chemical substance within the artificial organ system with a microscope; and (c) observing the chemical substance within the artificial organ system by microscope in order to determine the characteristics of the transport mechanisms of the chemical substance.

As used herein, "processing" means placing the artificial organ system into a tissue fixing reagent, embedding the system in either paraffin or plastic, sectioning the system and placing the sections on either glass slides or metal grids, staining the system and observing the system in either a light or electron microscope. The artificial organ system can also be prepared for histochemical and fluorescence microscopy, using protocols well known in the art.

The present invention is more particularly described in the following examples which are intended as illustrative only since numerous modifications and variations will be apparent to those skilled in the art.

EXAMPLES

A Tissue Culture Bilayer Model of Bacterial Infection

Attachment and invasion by meningococci were examined using several epithelial cell monolayers including HecIB, HEp-2, and HeLa cells. While the bacteria were found to invade all cell types, larger numbers of bacteria were found to attach to and invade the HecIB cells. Based on these preliminary data HecIB cells, an endometrial carcinoma cell line frequently used to study gonococcal attachment and invasion, were used as the epithelial layer of the artificial organ culture. The human microvascular endothelial cell line, HMEC-1 was used as the second layer in this model. Using this system a variety of meningococcal strains including epidemic and sporadic case and carrier isolates, strains with and without pili or capsule, and other spontaneous and transposon-induced mutants were examined. Marked differences that exist among the strains in terms of their ability to pass through the bilayer may correlate with differences in virulence. Microscopic evidence indicates that the bacteria are passing through the layer of epithelial cells and through the membrane to the endothelial layer below without causing damage to the epithelial cells. This resembles what is observed in the human host where extensive tissue damage in the nasopharynx is only rarely reported. The present examples describe the examination of several other genera of bacteria whose interaction with eucaryotic cells has been well characterized. Bilayer assay results among strains of *Haemophilus influenzae* type b, *Salmonella typhimurium*, *Shigella flexneri*, and *Yersinia enterocolitica* showed differences but were consistent with previously published invasion and attachment results.

Bilayer (Artificial Organ Culture) Construction

A Transwell-COL™ insert (Costar, Cambridge, Mass.) with 3.0 μm pores was placed in each well of a six well tissue culture cluster plate. HMEC-1 endothelial cells ($1 \times 10^5$ cells/ml) were suspended in endothelial basal medium (EBM) (Gibco, Grand Island, N.Y.) with 7% fetal bovine serum (FBS) and 3 ml aliquots were added to each upper chamber (above the membrane). EBM+7% FBS (without cells) was added to the lower chamber (beneath the Transwell insert) in sufficient quantity to completely cover the membrane. The cells were incubated at 37° C. in 5% $CO_2$ for eight days allowing formation of a continuous monolayer. The cell suspension in the upper chamber and the medium in the lower chamber were removed and a like suspension of HecIB epithelial cells in EMEM (Eagles Minimal Essential Medium) was added to the upper chamber. Fresh EBM tissue culture medium was added to the lower chamber. At seven day intervals all medium was removed from both chambers and replaced with fresh EBM. As demonstrated by histological analysis, the bilayer was completely formed and ready for use 15–20 days after the addition of the epithelial cell layer. Fluorescence microscopy was used to determine the orientation of the cell layers in relation to the membrane. All cells were stained with Bodipy 581/591 phalloidin (Molecular Probes, Inc., Eugene, Oreg.) which stained the F actin of both cell layers. The cells were then stained with antibodies to the epithelial membrane antigen (DAKO, Carpinteria, Calif.) labelled with fluorescein isothiocyanate. Actin in all cells fluoresced red while the outer membrane of the epithelial cells fluoresced green.

When epithelial cells were added to the chambers after the endothelial monolayer was established on the top side of the membrane, the endothelial cells migrated through the 3 μm pores to the basal (endothelial) side of the membrane where they remained. The artificial membrane appeared to function as a basement membrane for both the epithelium and the endothelium. As the epithelial cells grew, this layer became several cells thick and, in some cases, the cells differentiated into a columnar or cuboidal form. Determination of bilayer integrity (confluency) was based on microscopic observation and on the minimal passage of inert uncharged beads through the bilayer system. Approximately $10^7$ colored polystyrene beads, 0.833 μm in diameter, (Seradyn, Indianapolis, Ind.) were added to 1 ml of tissue culture medium in the upper chamber. After three hours, the medium in the lower chamber was removed and centrifuged. Less than 0.01% of beads were observed to have passed into the lower chamber, suggesting that no gaps as large as 0.833 μm existed in the cell layers.

Thus, an important feature of the invention is the modeling of cell-to-cell communication between and among epithelial and endothelial cells that occurs in vivo. Cellular communication occurs in the bilayer model as evidenced by the fact that when epithelial cells are added to the system after the endothelial monolayer is established on the apical side of the membrane, the endothelial cells migrate through the 3 μm pores to the basal side of the membrane where they re-establish a monolayer. The central membrane appears to function as a basement membrane for both the epithelium and the endothelium.

Bacterial Strains

Strains of *Neisseria meningitidis* obtained from patients with clinical disease were designated as case strains, and strains from asymptomatic carriers were designated as carrier strains. Serogroup A strains were from an outbreak in Kenya: case strains F8187, F8188, F8229 and carrier strains F8239, F8240, F8243. Serogroup B case strain NMB was from Pennsylvania (25) and M7 (25) was a Tn916 induced mutant of NMB. Code 2 was a serogroup B case strain from Georgia. FAM 18+ and FAM 18– were, respectively, piliated and nonpiliated serogroup C strains (originally obtained from Janne Cannon, University of North Carolina, Chapel Hill, N.C., and provided by David Stephens, Emory University, Atlanta, Ga.). Strains B92–2177, CI–416b, G1161, G7026, and G8052 were serogroup C case strains from the United States and Canada. G2881, G2938, R251, and B534 were nongroupable meningococcal carrier strains from the United States. (All bacterial strains were maintained at the Centers for Disease Control and Prevention, Atlanta, Ga.). *Haemophilus influenzas* type b (KC 1050), *Salmonella typhimurium* (B2247), *Shigella flexneri* (3015–94), and *Yersinia enterocolitica* (3468–85) were patient isolates from the culture collections of the Division of Bacterial and Mycotic Diseases, Centers for Disease Control and Prevention, Atlanta, Ga. All strains were stored in Luria Bertani broth with 20% glycerol at −70° C. Meningococcal strains were grown on chocolate agar plates (BBL, Cockeysville, Md.) at 37° C. in 5% $CO_2$; other strains were grown on heart infusion agar with 5% rabbit blood (BBL, Cockeysville, Md.) at 37° C. The proper functioning of the organ system of the claimed invention is not dependent upon the particular organism being studied.

Bilayer Infection and Transport Studies

The inoculation of a single bilayer chamber or of several identical chambers allows study of a number of virulence characteristics including attachment, invasion, transcytosis and exit or extracellular passage through tight junctions. One can also examine the effect of various inhibitors of bacterial or host cell function or of antibodies on each of these aspects of the infectious process. Thus, it is possible to study the effect of inhibitors of host cell microfilament and microtubule function, pinocytosis, and protein synthesis, and exactly how the inhibitors interfere with the infectious process.

Before infection of the artificial organ system, all medium was removed, the bilayer was washed once with phosphate-buffered saline, and EBM with 15% human serum was added (1 ml in the upper chamber, 1 ml in the lower chamber). In some experiments cytochalasin D (5 μg/ml) was added to the medium in both chambers 30 minutes prior to infection and maintained throughout the experiment. Trypan blue assays of cell viability in HecIB and HMEC monolayers showed minimal cell death after 21 hours in the presence of like amounts of cytochalasin D.

Bacteria were grown overnight on chocolate agar and suspended in tissue culture medium to an $OD_{600}$=0.5, or $10^8$–$10^9$ bacteria/ml. This suspension was diluted to add approximately $10^3$ bacteria to each upper chamber, and each dish was incubated at 37° C. in 5% $CO_2$. At time points of 15, 18, and 21 hours after infection, medium was removed from each lower chamber and dilutions were spread on agar plates to determine the number of viable bacteria passing through the bilayer. Other methods of counting bacterial cells can also be used without any expected difficulty. The first assay, performed 15 hours following infection, provided the number of bacteria that had been able to travel through both cell layers and the porous membrane in this time period. Fresh medium was then added to the lower chamber. The second assay at 18 hours measured the number of bacteria emerging from the cell layers in the preceding three hours; these may have travelled the entire distance in this time or may have been making their way through the tissue during most of the 18 hours. Likewise, the number of viable organisms found at the third time point 21 hours after infection showed the number of organisms emerging from the tissue during the final three hours of the assay. Because these last numbers were more variable from strain to strain, they were the numbers routinely used to compare strains. In some strains virtually no bacteria were able to make their way through the cell layers until the 21 hour time point. Samples of the upper chamber contents were plated at selected time points to determine bacterial growth over the course of the experiment.

Results of bacterial transport rate studies are described below and summarized in Table 1. Replication in the upper chamber over 21 hours resulted in numbers ranging from $1.1 \times 10^7$ to $2.5 \times 10^9$. Among the serogroup A strains tested, numbers of viable organisms in the lower chamber at 21 hours ranged from $2 \times 10^7$ to $2.5 \times 10^8$. There appeared to be no significant difference between case and carrier strains in this group. The exception was a single carrier strain, F8239, with an average viable count of $2.5 \times 10^4$. Like the serogroup A strains, serogroup B case strain Code 2 showed viable counts above $10^8$ in the lower chamber at the 21 hour time point. NMB, a case isolate multiply passaged on artificial media, averaged $7.6 \times 10^6$ while the transposon-induced mutant of strain NMB, M7, was considerably lower, at $2.6 \times 10^3$. Within serogroup C, the piliated and nonpiliated variants of FAM 18 gave similar numbers greater than $10^7$ in the lower chamber. Numbers from other serogroup C case isolates ranged from $1.7 \times 10^5$ to $5.5 \times 10^7$. Among the nongroupable strains tested, numbers ranged from $6.9 \times 10^2$ to $1.7 \times 10^5$, thus generally lower than any of the groupable strains, but not statistically different as a group. Also shown in Table 1 are the ratios of lower chamber (LC) to upper chamber (UC) numbers which indicate the percentage of each bacterial population which was able to move through the cell layers during the final 3 hours of the 21 hour infection. This ratio is a measure of invasiveness in this model and allows comparison and grouping of strains based on these numbers.

Following the assay at 21 hours, all medium was removed and the insert was fixed for 4–12 hours in 10% neutral buffered formalin. Each chamber was removed with forceps from the formalin and placed on its own 47 mm 0.2 μm Vericel™ (Gelman Sciences, Ann Arbor, Mich.) membrane filter dampened with distilled water. A sharp-pointed scalpel blade was used to cut the artificial organ system away from the inside of the chamber, at the same time cutting all the way through the underlying Vericel membrane. Supported by the larger Vericel membrane, the cell layers and artificial membrane were compactly rolled up with forceps. The original upper (apical/epithelial) side of the Costar membrane thus reliably corresponded to its concave surfaces once it was rolled up. Two 2 mm cross sections were cut from the middle of the roll with a sharp blade and placed on edge on a square piece of lens paper. The lens paper was then folded over the two membrane ensembles and the wrapped specimens were placed in a perforated plastic cassette containing the appropriate pathology accession number. Cassettes were immersed in 70% ethanol for transfer. Specimens were processed for 16 hours in a Fisher Histomatic™ (Fisher Scientific, Pittsburgh, Pa.) tissue processor, embedded in Polyfin™ (Triangle Biomedical Sciences, Durham, N.C.) embedding medium, and sectioned at 4 μm on a Leitz 1512 microtome. Blocks were trimmed deeply enough to compensate for any retraction of the cell layer from the edges of the membranes. Sections were floated on a 44° C. water bath, collected on 3×1 inch glass microscope slides coated with aminosilane (A. Daigger and Co., Inc., Wheeling, Va.), warmed in a 65° C. paraffin oven for 20 minutes, and stained with Harris' hematoxylin and eosin. For species other than *Neisseria meningitidis* a Steiner silver stain was also done.

A time course experiment in which bilayer chambers were removed for microscopic observation at 2, 12, 15, 18, and 22 hours after infection showed that meningococci migrated from the apical surface down through and between the epithelial cells to the basal surface. Observed 12 hours after infection, the bacteria were seen in contact with the upper surface of the epithelial cells. Electron microscopic observation suggested that this attachment was via actin pedestals. At points along the epithelial surface, meningococci began to invade between adjacent cells, either moving in to fill an existing indentation or forcing a break in the cellular tight junction. After 15 hours, extracellular bacteria were often observed extending in vertical columns entirely through several layers of separated cells. By electron microscopy, bacteria were seen between cells disrupting the integrity of the host cell tight junctions. In some cases where the epithelium had become stratified, the bacteria travelled in a lateral direction spreading between the stacked layers of epithelial cells. In addition, throughout the time course experiment meningococci were seen internalized by the host epithelial cells and appeared to be within vacuoles, perhaps moving through the cell towards the apical surface of the membrane. Meningococci emerged from the epithelial cell layer between 15 and 22 hours following infection. Having passed through the epithelial layer by either the intracellular or intercellular route, the bacteria were then able to pass through the porous membrane and into and through the endothelial layer beneath, probably via the same mechanisms, finally emerging in large numbers on the surface of the endothelial cells facing the bottom of the culture well in the lower chamber. Viable count data suggest that the majority of bacteria travelled within the cells of the epithelial layer since in the presence of cytochalasin D, an inhibitor of host cell phagocytosis, numbers of bacteria passing through the bilayer were reduced by 95–99%.

To compare the passage of meningococci through the bilayer system with that of other bacteria whose attachment and invasion mechanisms have been well characterized, the same protocol was used to examine passage of *Haemophilus influenzae* type b, *Salmonella typhimurium*, *Shigella flexneri*, and *Yersinia enterocolitica*. The results are summarized in Table 2. Numbers of organisms reaching the lower chamber between 18 and 21 hours following infection varied from $5 \times 10^3$ for *Y. enterocolitica* to $1.5 \times 10^8$ for *S. typhimurium* with numbers of *H. influenzae* and *S. flexneri* falling between these two.

Mechanisms of Pathogenesis

A number of bacterial factors have been examined to determine their importance in meningococcal pathogenesis. One of the most studied has been the role of pili in the attachment of *Neisseria meningitidis* to human epithelial and endothelial cells (16, 27). Many consider pili the most important mediator of the attachment which must occur before invasion can take place (21). However, as Stephens and McGee (22) pointed out in an earlier study, the extreme difference in pathogenicity between commensal neisseriae and meningococci suggests virulence mechanisms other than pili. This study has shown that the serogroup C strain FAM18 and its nonpiliated variant pass through the bilayer system in almost equal numbers. Also, the serogroup A strain F8239 has been shown to be the only strain other than piliated FAM18 that is consistently positive in a hemadsorption assay, a characteristic that correlates with the expression of pili on the meningococcal surface (13). F8239, however, passes through the bilayer in much lower numbers than any of the other serogroup A strains. In addition to pili, data suggest that the class 5 outer membrane proteins are also involved in initial attachment (1, 31). However, while cell attachment is necessary, it is not sufficient to cause disease (16); other factors must play the major role in invasion and transcytosis. One of these factors which plays a significant role in meningococcal virulence is the polysaccharide capsule. While encapsulation appears to be necessary for survival in the bloodstream, more efficient attachment to epithelial and endothelial cells may occur with strains deficient in capsule; the capsule may mask pili binding sites and interfere with attachment (11, 22, 24, 28, 29).

However, in the present bilayer system there was a marked decrease in the number of bacteria passing through and into the lower chamber when the bacteria were capsule deficient or altered in capsule production. The first six strains listed in Table 1 are either nongroupable isolates or capsule deficient mutants, including serogroup A strain F8239 which does not agglutinate in the presence of group A capsular antisera and the transposon-induced mutant of NMB, M7, which does not produce group B capsular polysaccharide. In terms of their invasiveness, these six strains are either much less than or equal to the least invasive of the remainder of the strains listed which are all groupable and therefore encapsulated.

Many, if not all, invasive microbes encode several separate pathways for entry into cultured cells (6). By adding cytochalasin D, an inhibitor of host phagocytosis, to the system, many fewer organisms were found to be able to pass through the bilayer. This would support the previous epithelial and endothelial monolayer studies of Virji et al. (31) and could suggest that the intracellular route may be the primary route of passage. However, microscopic examination in this study revealed long columns of meningococci that appeared to be intercellular rather than within vacuoles. In electron micrographs, many more meningococci were seen between cells than within them and these intercellular organisms appeared to be, at least temporarily, disrupting the cellular tight junctions. Stephens and Farley (21) and Virji et al. (28) found that infection with meningococci produced cytotoxic effects after infection characterized by breakdown of epithelial cell tight junctions. Thus, this intercellular pathway, primarily used by the encapsulated bacteria, may be the alternate route taken by the meningococci. Although this route has been observed in *Haemophilus influenzae* type b passage through the nasopharyngeal organ culture (21), it has never been described in previous models for *Neisseria meningitidis*. Cytochalasin D, which acts on host microfilaments, may interfere with contraction of the meshwork of microfilaments which regulate tension at the intercellular epithelial surface (5a) thus limiting bacterial passage. The addition of cytochalasin D prior to infection significantly reduced the numbers of organisms passing through the bilayer indicating that host cell function is important in meningococcal invasion and transcytosis.

An additional cytotoxic effect of the bacterial infection may be the deterioration of the endothelial layer observed microscopically 21 hours after addition of the meningococci. In Huvec monolayers, Virji et al. also saw disruption of intercellular junctions, changes in normal cell morphology, and some loss of cells from the monolayers (28). This damage is consistent with the extensive damage to the endothelial lining of the blood vessels seen in autopsy material from human disease (9).

In a further effort to understand the mechanisms involved in meningococcal passage and, ultimately, those used by all invasive bacteria, the passage through the bilayer model of several other organisms, whose attachment and invasion mechanisms have been well characterized, was examined. As stated previously, *H. influenzae* type b (Hib) is known to invade the epithelium by passing through the intercellular tight junctions. These cells passed rapidly through the artificial organ culture, with $3 \times 10^7$ organisms reaching the lower chamber in the first 15 hours after Hib infection. The invasive enteric pathogens *Salmonella typhimurium* and *Yersinia enterocolitica* are phagocytized by eucaryotic cells and remain trapped in the phagocytic vacuole while *Shigella flexneri* enters the cell and subsequently lyses the phagocytic vacuole to gain access to the host-cell cytoplasm (17). Using polarized MDCK monolayers, Finlay et al. found that *Salmonella choleraesuis* cells transcytose the monolayer by four hours after infection and reach a maximal rate of 14 bacteria/MDCK cell per hour after nine hours; *S. typhimurium* behave nearly identically (7). Although the previous studies looked only at monolayers, in this study, similar numbers were seen emerging from the bilayer after infection with *S. typhimurium*, an average of $2.5 \times 10^6$ at the 15-hour time point. Intracellular trafficking of Yersinia and Shigella may be different from Salmonella since far fewer organisms make their way through the bilayer in the first 15 hours.

TABLE 1

Passage of *Neisseria meningitidis* through tissue culture bilayer (21 hours after infection)

|  | Lower Chamber[a] (LC) | Upper Chamber[b] (UC) | Ratio (%) LC:UC |
|---|---|---|---|
| Serogroup A | | | |
| F 8187 | $2.5 \times 10^8$ | $1.5 \times 10^9$ | 16.7 |
| F 8188 | $9.6 \times 10^7$ | $2.0 \times 10^9$ | 4.8 |
| F 8229 | $1.0 \times 10^8$ | $1.1 \times 10^9$ | 9.1 |
| F 8239 | $2.5 \times 10^4$ | $3.2 \times 10^7$ | 0.08 |
| F 8240 | $2.0 \times 10^7$ | $8.8 \times 10^8$ | 2.3 |
| F 8243 | $1.3 \times 10^8$ | $2.5 \times 10^9$ | 5.2 |
| Serogroup B | | | |
| NMB | $7.6 \times 10^6$ | $4.5 \times 10^8$ | 1.7 |
| M7 | $2.6 \times 10^3$ | $1.1 \times 10^7$ | 0.02 |
| Code 2 | $2.0 \times 10^8$ | $2.5 \times 10^8$ | 80.0 |
| Serogroup C | | | |
| FAM 18+ | $2.3 \times 10^7$ | $4.0 \times 10^8$ | 5.7 |
| FAM 18− | $5.1 \times 10^7$ | $7.0 \times 10^8$ | 7.3 |
| CI-416b | $4.1 \times 10^5$ | $1.1 \times 10^9$ | 0.04 |
| G 7026 | $5.5 \times 10^7$ | $2.2 \times 10^9$ | 2.5 |
| G 8052 | $1.7 \times 10^5$ | $4.5 \times 10^8$ | 0.04 |
| G 1161 | $3.0 \times 10^5$ | $6.0 \times 10^8$ | 0.05 |
| B92-2177 | $2.4 \times 10^6$ | $4.0 \times 10^8$ | 0.6 |
| Nongroupable | | | |
| G 2881 | $6.9 \times 10^2$ | $4.6 \times 10^8$ | <.01 |
| G 2938 | $1.7 \times 10^5$ | $2.0 \times 10^9$ | 0.01 |
| B 534 | $6.8 \times 10^3$ | $1.0 \times 10^8$ | <.01 |
| R 251 | $1.7 \times 10^5$ | $2.5 \times 10^9$ | <.01 |

[a]Number of bacteria reaching lower chamber between 18 and 21 hours post-infection (numbers are an average of at least three trials)
[b]Each chamber infected with ~$10^3$ bacteria

TABLE 2

Passage through tissue culture bilayer

|  | Lower Chamber (LC) | Upper Chamber[b] (UC) | Ratio (%) LC:UC |
|---|---|---|---|
| *H. influenzae* type B | $9.4 \times 10^7$ | $2.5 \times 10^9$ | 3.80 |
| *S. typhimurium* | $1.5 \times 10^8$ | $9.5 \times 10^8$ | 15.80 |
| *S. flexneri* | $8.0 \times 10^5$ | $3.5 \times 10^8$ | 0.23 |
| *Y. entero* | $5.0 \times 10^3$ | $9.0 \times 10^7$ | <.01 |

[a]Number of bacteria reaching lower chamber between 18 and 21 hours post-infection
[b]Each chamber infected with ~$10^3$ bacteria

REFERENCES

1. Achtman, M., Wall, R. A., Bopp, M., Kusecek, B., Morelli, G., Saken, E., and Hassan-King, M. 1991. Variation in class 5 protein expression by serogroup A meningococci during a meningitis epidemic. J. Infect. Dis. 164:375–382.
2. Apicella, M. A. 1991. *Neisseria meningitidis*: pathogenesis and immune response, p.75–83. In H. P. Lambert (ed.), Infections of the central nervous system. B. C. Decker Inc., Philadelphia.
3. Arko, R. J. 1989. Animal models for pathogenic Neisseria species. Clin. Microbiol. Rev. 2 (suppl.):S56–S59.
4. Bessen, D., and Gotschlich, E. C. 1986. Interactions of gonococci with HeLa cells; attachment, detachment, replication, penetration, and the role of protein II. Infect. Immun. 54:154–160.
5. Buddingh, G. J., and Polk, A. 1937. Meningococcus infection of chick embryo. Science. 86:20–21.
5a. Burkitt, H. G., Young, B., and Heath, J. W. 1993. Wheater's functional histology, a text and colour atlas, 3rd ed., p.84. Churchill Livingstone, Edinburgh.
6. Falkow, S. 1991. Bacterial entry into eukaryotic cells. Cell. 65:1099–1102.
7. Finlay, B. B., Fry, J., Rock, E. P., and Falkow, S. 1989. Passage of Salmonella through polarized epithelial cells: role of the host and bacterium. J. Cell Sci. Suppl. 11:99–107.
8. Flexner, S. 1907. Experimental cerebrospinal meningitis in monkeys. J. Exp. Med. 9:142–166.
9. Hill, W. R., and Kinney, T. D. 1947. The cutaneous lesions in acute meningococcemia. JAMA. 134:513–518.
10. Holbein, B. E. 1981. Difference in virulence for mice between disease and carrier strains of *Neisseria meningitidis*. Can. J. Microbiol. 27:738–741.
11. McGee, Z. A., and Stephens, D. S. 1984. Common pathways of invasion of mucosal barriers by *Neisseria gonorrhoeae* and *Neisseria meningitidis*. Surv. Synth. Path. Res. 3:1–10.
12. Miller, C. P. 1933. Experimental meningococcal infection in mice. Science. 78:340–341.
13. Pinner, R. W., Spellman, P. A., and Stephens, D. S. 1991. Evidence for functionally distinct pili expressed by *Neisseria meningitidis*. Infect. Immun. 59:3169–3175.
14. Richardson, W. P., and Sadoff, J. C. 1988. Induced engulfment of *Neisseria gonorrhoeae* by tissue culture cells. Infect. Immun. 56:2512–2514.
15. Salit, I. E. 1984. Experimental meningococcal infection in neonatal animals: models for mucosal invasiveness. Can. J. Microbiol. 30:1022–1029.
16. Salit, I. E., and Morton, G. 1981. Adherence of *Neisseria meningitidis* to human epithelial cells. Infect. Immun. 31:430–435.

17. Sansonetti, P. J. 1993. Bacterial pathogens, from adherence to invasion: comparative strategies. Med. Microbiol. Immunol. 182:223–232.
18. Schwartz, B., Moore, P. S., and Brooms, C. V. (1989). Global epidemiology of meningococcal disease. Clin. Microbiol. Rev. 2 (suppl.):S118–S124.
19. Shaw, J. H. and S. Falkow. 1988. Model for invasion of human tissue culture cells by *Neisseria gonorrhoeae*. Infect. Immun. 56:1625–1632.
20. Stephens, D. S. 1989. Gonococcal and meningococcal pathogenesis as defined by human cell, cell culture, and organ culture assays. Clin. Microbiol. Rev. 2 (suppl.):S104–S111.
21. Stephens, D. S., and Farley, M. M. 1991. Pathogenic events during infection of the human nasopharynx with *Neisseria meningitidis* and *Haemophilus influenzas*. Rev. Infect. Dis. 13:22–33.
22. Stephens, D. S., and McGee, Z. A. 1981. Attachment of *Neisseria meningitidis* to human mucosal surfaces: influence of pili and type of receptor cell. J. Infect. Dis. 143:525–532.
23. Stephens, D. S., Hoffman, L. H., and McGee, Z. A. 1983. Interaction of *Neisseria meningitidis* with human nasopharyngeal mucosa: attachment and entry into columnar epithelial cells. J. Infect. Dis. 148:369–376.
24. Stephens, D. S., Spellman, P. A., and Swartley, J. 1993. Effect of the (α2–8)-linked polysialic acid capsule on adherence of *Neisseria meningitidis* to human mucosal cells. J. Infect. Dis. 167:475–479.
25. Stephens, D. S., Swartley, J. S., Kathariou, S., and Morse, S. A. 1991. Insertion of Tn916 in *Neisseria meningitidis* resulting in loss of group B capsular polysaccharide. Infect. Immun. 59:4097–4102.
26. Virji, M., and Everson, J. S. 1981. Comparative virulence of opacity variants of *Neisseria gonorrhoeae* strain P9. Infect. Immun. 31:965–970.
27. Virji, M., Alexandrescu, C., Ferguson, D. J. P., Saunders, J. R., and Moxon, E. R. 1992. Variations in the expression of pili: the effect on adherence of *Neisseria meningitidis* to human epithelial and endothelial cells. Mol. Microbiol. 6:1271–1279.
28. Virji, M., Kayhty, H., Ferguson, D. J. P., Alexandrescu, C., Heckels, J. E., and Moxon, E. R. 1991. The role of pili in the interactions of pathogenic Neisseria with cultured human endothelial cells. Mol. Microbiol. 5:1831–1841.
29. Virji, M., Kayhty, H., Ferguson, D. J. P., Alexandrescu, C., and Moxon, E. R. 1991. Interactions of *Haemophilus influenzas* with cultured human endothelial cells. Microb. Pathogen. 10:231–145.
30. Virji, M., Makepeace, K., Ferguson, D. J. P., Achtman, M., and Moxon, E. R. 1993. Meningococcal Opa and Opc proteins: their role in colonization and invasion of human epithelial and endothelial cells. Mol. Microbiol. 10:499–510.
31. Virji, M., Makepeace, K., Ferguson, D. J. P., Achtman, M., Sarkari, J., and Moxon, E. R. 1992. Expression of the Opc protein correlates with invasion of epithelial and endothelial cells by *Neisseria meningitidis*. Mol. Microbiol. 6:2785–2795.
32. Woods, J. P., Frelinger, J. A., Warrack, G., and Cannon, J. G. 1988. Mouse genetic locus Lps influences susceptibility to *Neisseria meningitidis* infection. Infect. Immun. 56:1950–1955.
33. Graham, M. D., Debra J., Alexander, M. D., J. Jeffrey, Remedios, M. S., Miguel 1991. Aortic Endothelial and Smooth Muscle Cell Co-Culture: An In Vitro Model of the Arterial Wall. Journal of Investigative Surgery. 4:487–494.
34. Taber's Cyclopedic Medical Dictionary, 12th Edition, F. A. Davis Co., Philadelphia, Pa.

What is claimed is:

1. An artificial organ system comprising an endothelial cell layer, an epithelial cell layer and an artificial noncellular microporous membrane disposed between and in direct contact with said endothelial cell layer and epithelial cell layer such that said membrane has an endothelial side and an epithelial side.

2. The artificial organ system of claim 1, wherein said system is contained in a vessel.

3. The artificial organ system of claim 1, wherein said endothelial cell layer consists of the cells of the human microvascular endothelial cell line, HMEC-1.

4. The artificial organ system of claim 1, wherein said epithelial cell layer consists of the cells of the human endometrial carcinoma cell line, HecIB.

5. The artificial organ system of claim 1, wherein said epithelial cell layer consists of the cells of the human cervical carcinoma cell line, HeLa.

6. The artificial organ system of claim 1, wherein said epithelial cell layer consists of the cells of the human larynx carcinoma cell line, Hep-2.

7. The artificial organ system of claim 1, wherein said artificial microporous membrane comprises pores ranging in diameter from 0.45 microns to 10 microns.

8. The artificial organ system of claim 7, wherein said artificial microporous membrane is a polycarbonate membrane.

9. The artificial organ system of claim 8, wherein said artificial microporous membrane is coated with a biocompatible material.

10. The artificial organ system of claim 9, wherein said artificial microporous biocompatible material is selected from the group consisting of collagen, laminin, proteoglycan, vitronectin, fibronectin, poly-D-lysine and polysaccharide.

* * * * *

UNITED STATES PATENT AND TRADEMARK OFFICE
Certificate

Patent No. 5,695,996                 Patented: December 9, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Frederick D. Quinn, Decatur, GA; Kristin A. Birkness, Atlanta, GA; and Edwin W. Ades, Atlanta, GA.

Signed and Sealed this Nineteenth Day of September, 2000.

MICHAEL G. WITYSHYN
*Supervisory Patent Examiner*
Art Unit 1651